United States Patent
Qu et al.

(10) Patent No.: US 7,556,605 B2
(45) Date of Patent: Jul. 7, 2009

(54) METHODS FOR DETERMINING ELASTIC AND VISCOELASTIC PROPERTIES OF SKIN

(75) Inventors: Di Qu, Ada, MI (US); Gurinder Paul S. Seehra, Grand Rapids, MI (US); Christopher J. Masotti, East Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 30 days.

(21) Appl. No.: 11/906,198

(22) Filed: Oct. 1, 2007

(65) Prior Publication Data

US 2008/0087098 A1   Apr. 17, 2008

Related U.S. Application Data

(60) Provisional application No. 60/850,917, filed on Oct. 11, 2006.

(51) Int. Cl.
*A61B 5/103* (2006.01)
*G01L 1/00* (2006.01)
*G01N 3/08* (2006.01)
*A61B 5/117* (2006.01)

(52) U.S. Cl. .......................... 600/587; 73/760; 73/788; 73/837

(58) Field of Classification Search ................. 600/587; 73/849, 837, 760, 788
See application file for complete search history.

(56) References Cited

U.S. PATENT DOCUMENTS

| | | | | |
|---|---|---|---|---|
| 4,976,272 A | * | 12/1990 | Bazin et al. ................. | 600/587 |
| 5,054,502 A | * | 10/1991 | Courage ..................... | 600/587 |
| 5,278,776 A | * | 1/1994 | Fisher et al. ................. | 600/587 |
| 5,379,235 A | * | 1/1995 | Fisher et al. ................. | 600/587 |
| 5,706,815 A | * | 1/1998 | Sarvazyan et al. ........... | 600/438 |
| 2008/0234607 A1 | * | 9/2008 | Hunter-Jones et al. ....... | 600/587 |

OTHER PUBLICATIONS

Escoffier et al. "Age-Related Mechanical Properties of Human Skin: An In Vivo Study" The Journal of Investigative Dermatology, vol. 93, No. 3. Sep. 1989. pp. 353-357.*
Cua et al. "Elastic Properties of Human Skin: Relation to Age, Sex and Anaotmical Region" Archive of Dermatological Research, pp. 283-288.*
BTC-2000. http://www.srli.com/technologies/BTC2000.html.*

* cited by examiner

*Primary Examiner*—Lisa M Caputo
*Assistant Examiner*—Jonathan Dunlap
(74) *Attorney, Agent, or Firm*—Brinks Hofer Gilson & Lione; G. Peter Nichols

(57) ABSTRACT

The invention relates to methods of measuring the overall elasticity of skin and determining the portion of the overall elasticity that is due to elastic properties and the portion of overall elasticity that is due to viscoelastic properties of the skin and correlating the results of the measurement to an individual's chronological age. The invention also relates to methods of measuring improvements in a person's skin health by measuring elasticity before, during and after human clinical trials of topical and/or oral treatment compositions. The parameters for determining elasticity are based on areas that are defined on a deformation/relaxation curve and require that an inflection point be determined for each skin sample analyzed.

7 Claims, 25 Drawing Sheets

METHODS FOR DETERMINING ELASTIC AND VISCOELASTIC PROPERTIES OF SKIN

RELATED APPLICATIONS

This application claims priority to and benefit of U.S. Provisional Application No. 60/850,917, entitled Methods For Determining Elastic and Viscoelastic Properties of Skin, by Di Qu, et. al. filed Oct. 11, 2006.

FIELD OF THE INVENTION

The invention relates to methods of measuring the overall elasticity of skin and determining the portion of the overall elasticity that is due to elastic properties, and the portion of overall elasticity that is due to viscoelastic properties of the skin, and correlating the results of the measurement to an individual's chronological age. The invention also relates to methods of measuring improvements in a person's skin health by measuring elasticity before, during and after human clinical trials of topical and/or oral treatment compositions.

BACKGROUND OF THE INVENTION

Determination in vivo of dermal elasticity is complicated by morphological challenges such as subdermal fat and connective tissue. Analytical challenges also exist due to the viscoelastic nature of skin. Several devices are known to be useful in the analysis of physical properties of the skin. For example, a Cutometer device is frequently used for this purpose. However, the viscoelastic property of skin may not allow accurate measurements of dermal elasticity as measured by current, generally recommended Cutometer operation.

The Cutometer software is set to calculate overall elasticity, pure elasticity and a viscoelastic ratio based on linear parameters of the curve. During analysis of a person's skin, vacuum (a negative pressure) is applied to the skin for a short period of time (one second for instance) to achieve an extension of the skin. The vacuum is then released and the skin begins to recover from the deformation during the subsequent period of time known as relaxation. A curve, similar to FIG. 1, is plotted and depicts a deformation distance of the skin in millimeters (mm) along the vertical axis versus time, in seconds, along the horizontal axis.

According to current convention, overall elasticity is calculated by dividing Ua by Uf (Ua/Uf) where Ua is a linear measurement from a level maximum deformation that occurs in the extension curve to a level of recovery by the end of the relaxation or recovery curve. Uf is the maximum deformation of the skin that occurs during the analysis.

Pure elasticity is calculated by dividing Ur by Ue (Ur/Ue) where Ur is the steepest slope on the recovery side as determined by the Cutometer setting. In current practice, Cutometers are recommended by the manufacturer to measure Ur between 1 and 1.1 seconds. Ue is early deformation in the skin generally believed to correlate with the skin elasticity. According to Hooke's law of elasticity, Ue is directionally proportional to the negative pressure applied, which indicates the flexibility of the skin.

The viscoelastic ratio is calculated by dividing Uv by Ue (Uv/Ue), where Uv is Uf minus Ue.

Limitations of relying on the linear parameters as an indication of elasticity are twofold. First, there is an inaccurate description of the elastic properties of the skin. The second drawback is that viscous properties of the skin are also miscalculated. Toward a remedy to these drawbacks, the methods described herein identify an actual inflection point rather than rely on a set infection point identified by the software associated with the measurement device and use an area defined by the curve rather than a linear measurement of the curve to calculate skin properties.

SUMMARY OF THE INVENTION

The current invention is a method of determining skin elasticity by the steps of applying negative pressure to deform the skin and subsequently releasing the pressure to obtain a deformation/relaxation curve such as those produced by a Cutometer reading, then identifying an inflection point on the relaxation curve and an area associated with absolute recovery. The method involves defining an area associated with elastic recovery above the inflection point and later in time along the relaxation curve and defining an area associated with a viscoelastic recovery below the inflection point and later in time along the recovery curve. Calculation of a skin elasticity value or portion of elasticity due to viscoelasticity is calculated by manipulation of the areas defined within the curve.

A further embodiment of the invention comprises the steps of comparing an elasticity value to a database of known elasticity values compared to age of an individual, and determining an age of the individual.

Another embodiment of the method includes steps for determining the age of the individual from a database comparison is conducted prior to and then after treatment with a topically or orally administered agent for improving skin health.

The method further involves the area associated with absolute recovery as the area bounded on the left by a vertical representation of a maximum deformation of the skin; bounded on the top by a horizontal representation of the maximum deformation of the skin; and bounded on the bottom by a horizontal reference point to a position of the skin prior to deformation.

DETAILED DESCRIPTION OF THE INVENTION

Typically, devices such as a Cutometer are used to measure the elasticity of skin. The Cutometer used to generate the curves and results discussed herein are from a Cutometer model number 575 manufactured by Courage and Khazaka Electronic GmbH and available from ACADERM, Menlo Park, Calif.

Figure 1:
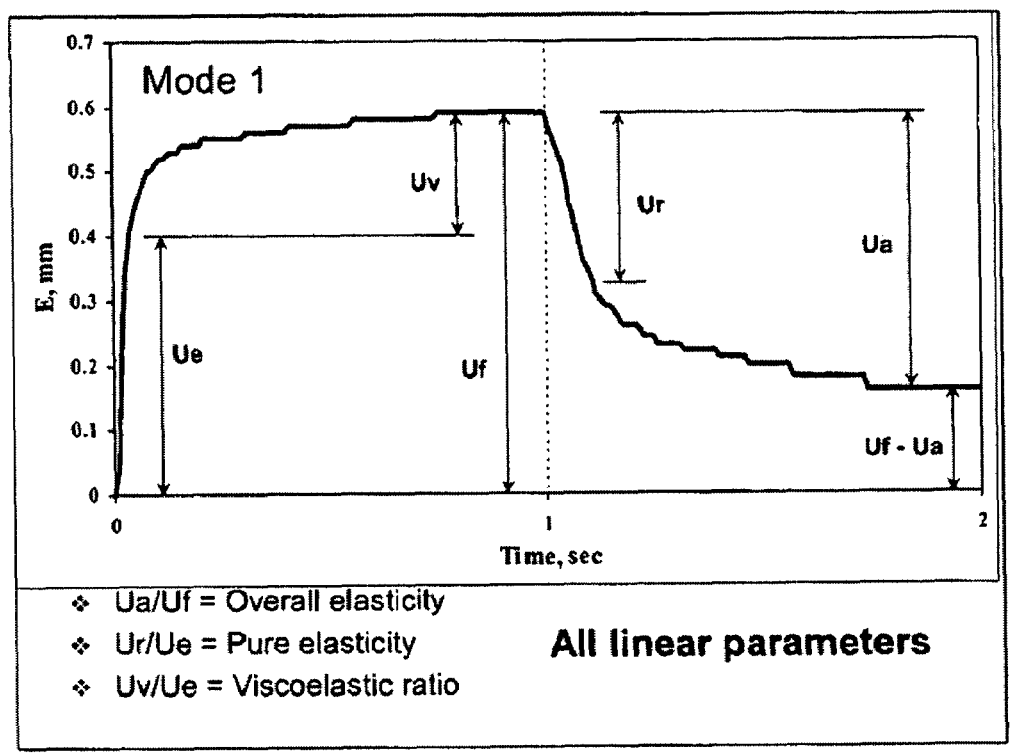
FIG. 1 is a prior art Cutometer reading depicting the deformation and relaxation curves of a skin sample with the linear parameters indicated.

FIG. 1 indicates the linear parameters used to calculate the elasticity and viscoelastic ratio. The limitations of relying on linear parameters as an indication of elasticity are inaccurate representations of the elastic viscous properties of the skin.

Figure 2:
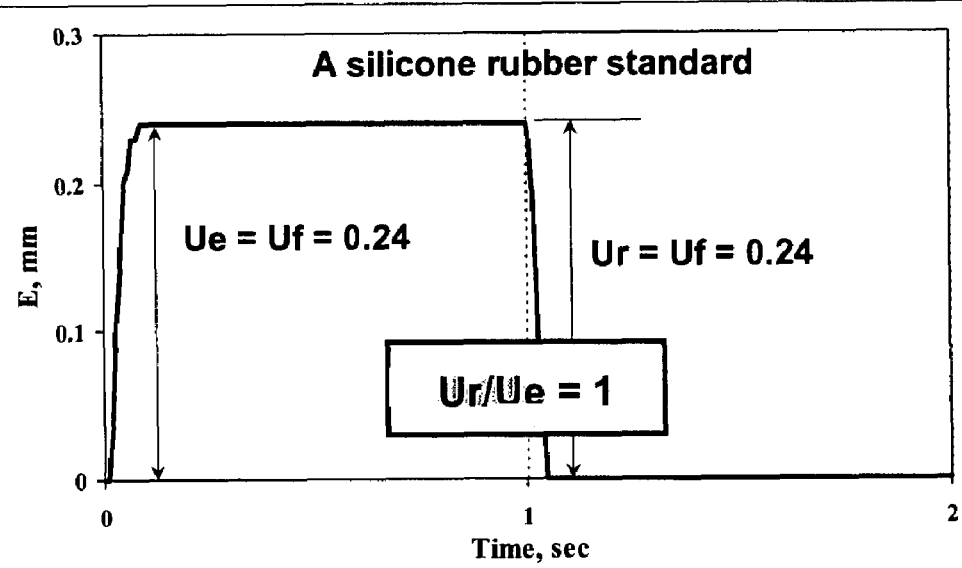
FIG. 2 is a deformation/relaxation Cutometer graph of a silicone rubber standard material.

FIGS. 2-7 and the corresponding discussion demonstrate the limitations of using linear parameters to measure elastic properties of materials. In FIG. 2, linear parameters of a silicone rubber standard material are depicted. Silicone standards are available in a Rex Durometers Test Block Kit, Rex Gauge Company, Inc., Buffalo Grove, Ill. Silicone is recognized as an ideal elastic material, therefore all of the deformation is expected to be due to the elastic properties of the material rather than due in part to any viscous properties a material may have. Therefore, Ue, the portion of the curve recognized as deformation due to elasticity, is equal to Uf, the total deformation distance achieved during the deformation phase of the analysis. During the recovery, or relaxation, period the material is returned to its original, pre-deformation position. Pure elasticity then, Ur/Ue, is equal to 1.0.

Figure 3:
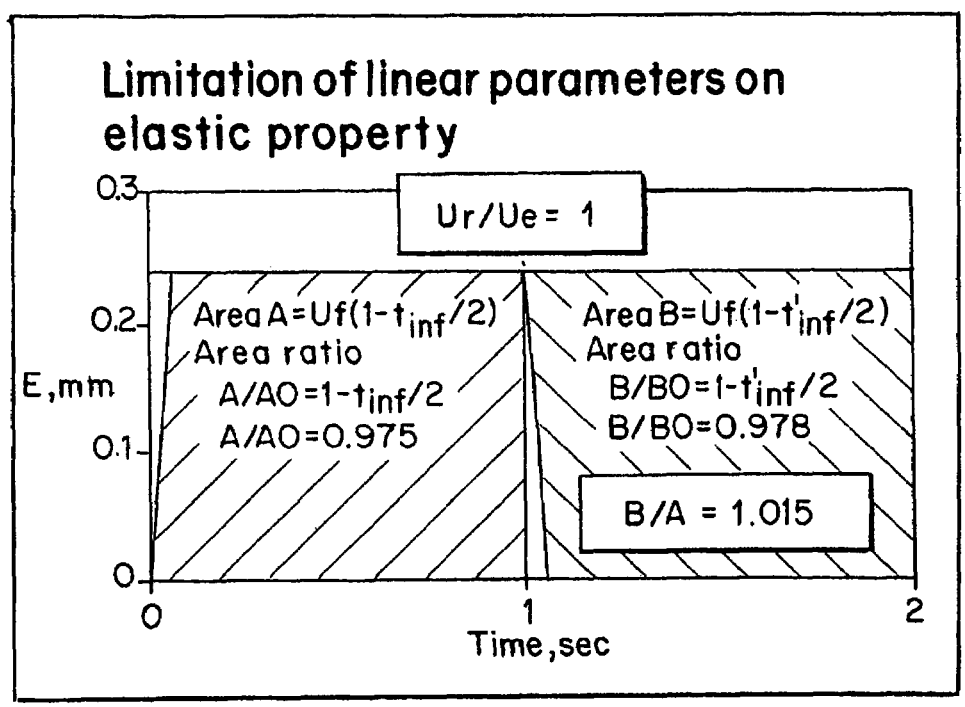
FIG. 3 is a deformation/relaxation Cutometer graph of a silicone rubber standard material depicting the areas under the curves.

However, because the measurement is taken over a period of time, the slopes of the extension, or deformation, curve and the recovery, or relaxation, curve represent a rate of deformation and rate of relaxation. These rates of deformation and relaxation are dependent upon the hardness of the material. The silicone material does not obtain maximum deformation instantaneously. Likewise, the material does not completely relax instantaneously. For an ideal material, the rough slope is considered a limitation of the testing instrument. Theoretically, the curve should show smooth lines. Use of a neat triangle as seen in FIG. 3 helps to simplify the calculations and facilitates estimation of the ideal property of the material. If the area under the deformation curve, A in FIG. 3, and the area under the relaxation curve, B in FIG. 3, are compared the resulting ratio of B/A is 1.015 which is different from the linear comparison, Ur/Ue, which resulted in a ratio of 1.0.

Figure 4:
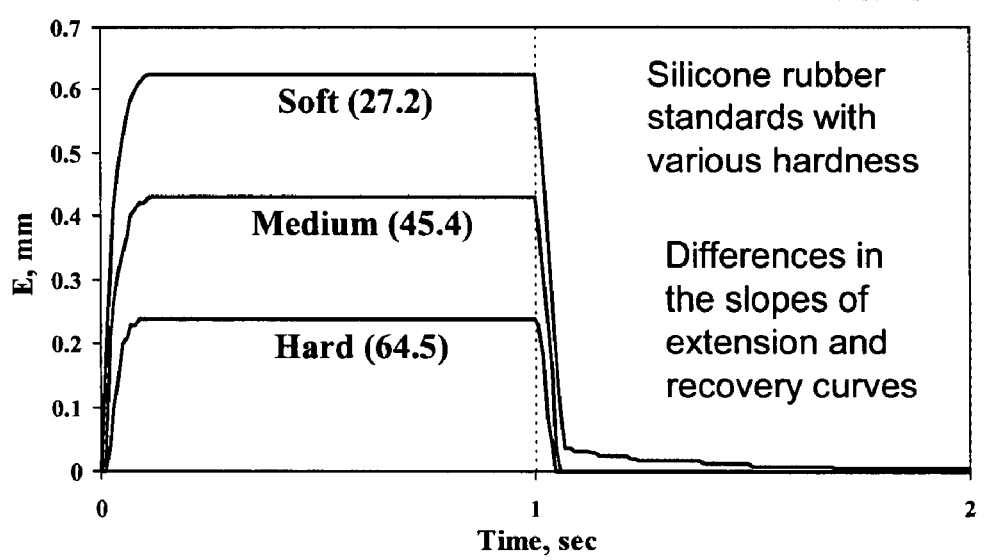
FIG. 4 is a deformation/relaxation Cutometer graph of silicone rubber standards of varying hardness.
Figure 5:
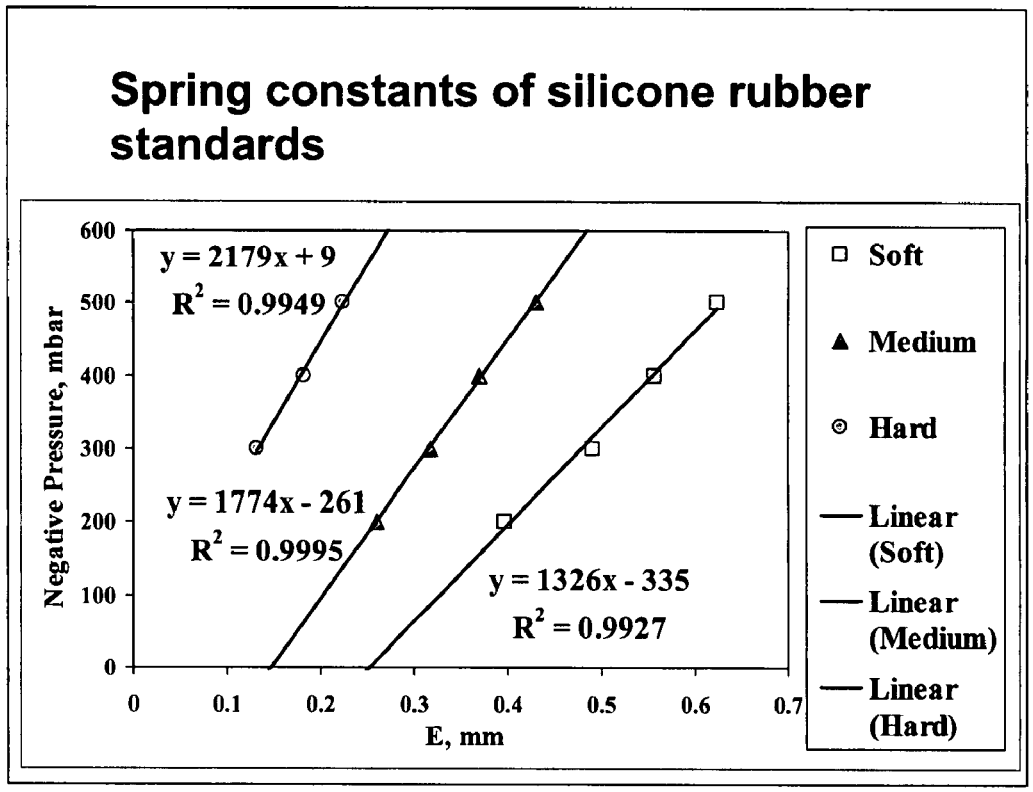
FIG. 5 is a graph depicting the spring constants of the silicone standards of FIG. 4.

FIG. 4 further demonstrates the role that hardness of a material may play in determining elasticity of a test material. The differences in the deformation and relaxation slopes as compared between silicones standards of varying hardness can be discerned upon visual examination. Following Hooke's law of elasticity, the spring constant, k, of each of the silicone rubber materials can be determined by subjecting each material to varying levels of negative pressure using the Cutometer. Results from such an analysis are depicted in FIG. 5. Spring constant, k, is derived from the equation $\sigma=E\epsilon$, where $\sigma$ is the tensile stress, E a proportional constant and $\epsilon$ the strain. In a simplified form, the equation can be expressed as $F=-k\,x$, where F is the force, x the distance the spring is elongated by, and k the spring constant. The spring constants for the materials shown in FIG. 5 are the values of 2179 (hard), 1774 (medium) and 1326 (soft).

Figure 6:
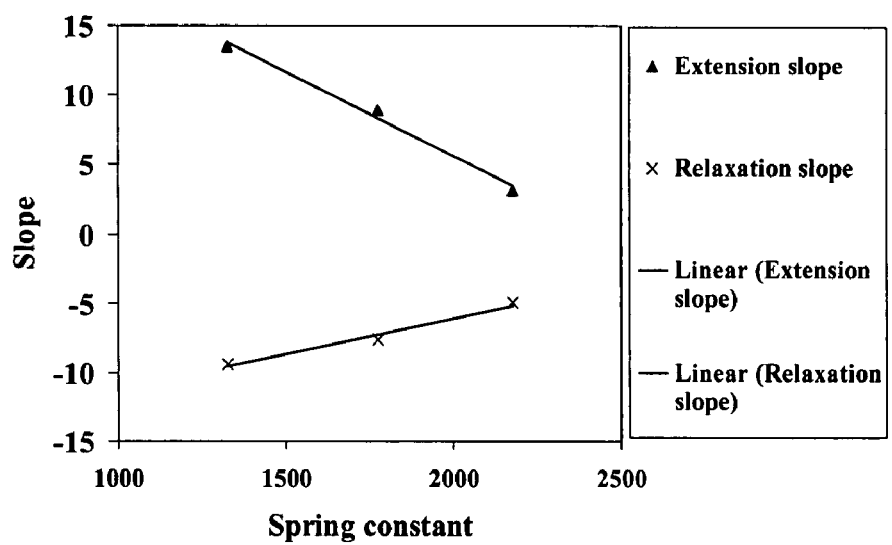
FIG. 6 is a graph comparing spring constant of the silicone materials to linear slope of the deformation and relaxation curves for each material.
Figure 7:
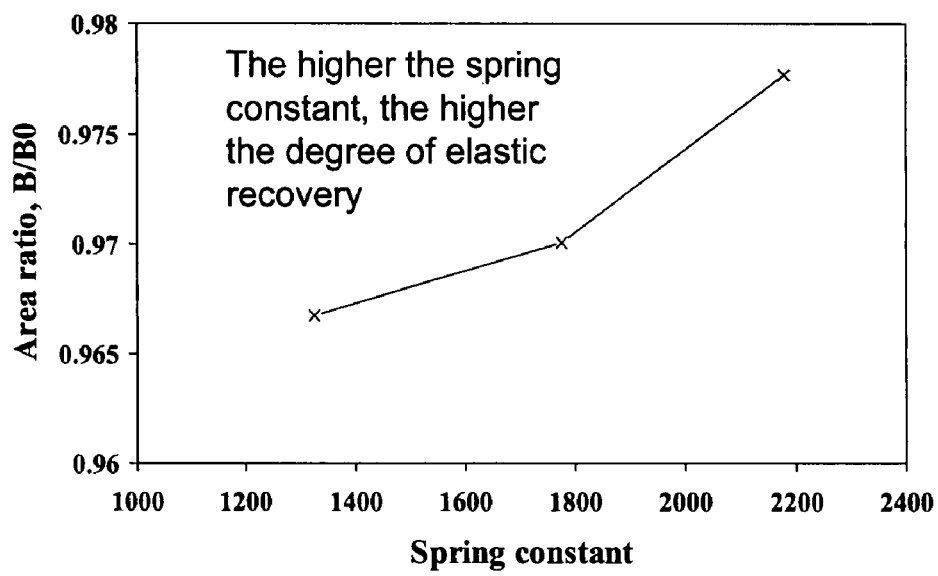
FIG. 7 is a graph comparing spring constant of the silicone materials to the area under the deformation curve for each material.

When the slopes of the linear deformation and relaxation curves are plotted against the spring constants for each of the silicone standards of varying hardness, strong correlations are observed. In FIG. 6, on the extension curve, hard material showed smaller value of slope because it was more difficult to stretch in the given time. On the relaxation curve, the absolute value of the slope was smaller as well, but it was shown by a bigger number which was caused by the downward direction of the slope. Simply put, the extension curve has a positive slope and the relaxation curve shows a negative slope. The absolute value determines big or small. When the slopes are normalized with the maximum extension of each rubber standard, a function between the spring constant and the degree of elastic recovery is obtained. Intuitively, hard material should retract quicker and therefore has a bigger absolute value of slope (steeper slope in negative direction). FIG. 6, however, showed an opposite effect. The reason was that the harder material had a smaller Uf value to start with. When you divide the relaxation slope with Uf, you bring all slopes to a unit extension deformation. The result of this is to normalize the slope to be able to compare among rubber standards with different hardness. After this normalization, the hard material did show a more complete recovery than the soft material which agrees with our intuition. This function indicates that the higher the spring constant, the greater the degree of elastic recovery as seen in FIG. 7. The elasticity calculations using linear parameters did not include the variation between the elastic properties of the silicone material standards.

Figure 8:
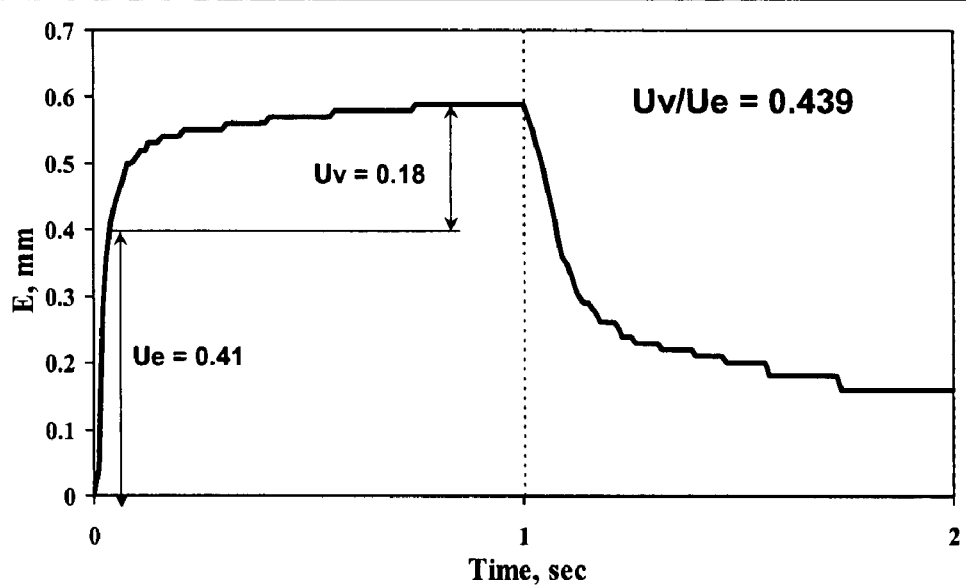
FIG. 8 is a deformation/relaxation Cutometer graph of a skin sample with linear parameters indicated.
Figure 9:
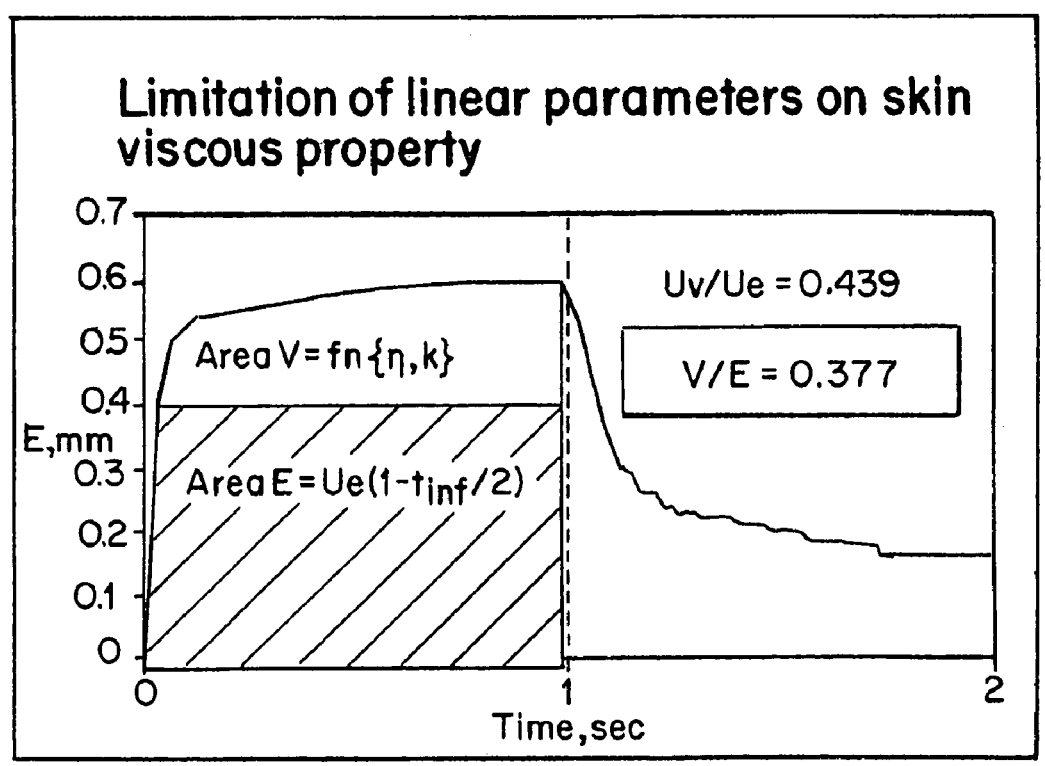
FIG. 9 is the deformation/relaxation Cutometer graph of a skin sample of FIG. 8 indicating areas that correspond to elastic deformation and viscous deformation.

FIGS. 8 and 9 and the corresponding discussion demonstrate the limitations of using linear parameters to measure viscous properties of materials. As discussed earlier, the current method for calculating viscoelastic ratio using linear parameters is by Uv/Ue. For the skin sample of FIG. 8, the viscoelastic ratio is 0.439. In FIG. 9, when the shape of the curve below the deformation curve is considered and the area is horizontally divided at the inflection point, the area under the deformation curve and below the inflection point (designated Area E in FIG. 9) represents the deformation due to elastic properties of the skin. The area under the deformation curve, but above the inflection point (designated Area V in FIG. 9) represents the deformation due to viscous properties of the skin. The early deformation in skin or material is due to elastic properties, while the later occurring deformation is due to viscous properties of the skin or material. The ratio of V/E equals 0.377. V/E is an area ratio corresponding to the linear ratio of Uv/Ue that equals 0.439 for this graph. The difference is accounted for in the shape of the curve which reflects the viscous properties of the skin. The viscoelasticity calculations that rely only on linear parameters of the curve did not include the variation of viscous properties of the materials.

Figure 10:
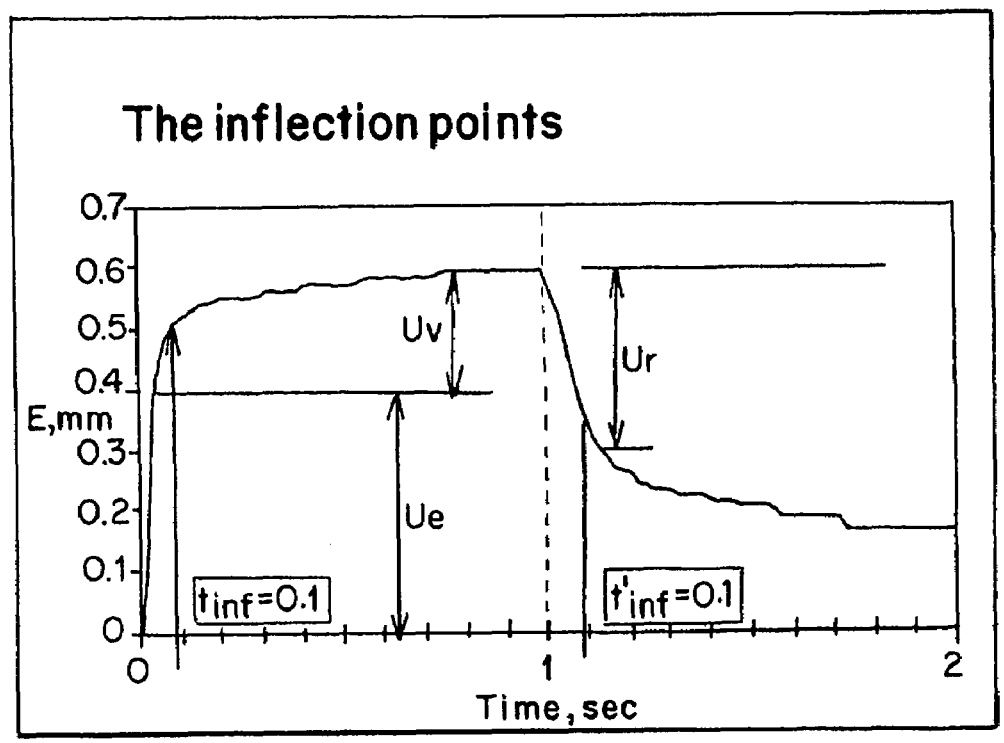
FIG. 10 is a deformation/relaxation Cutometer graph indicating set inflection points.

Inflection points are defined as a point on a curve where the slope changes. As mentioned earlier, Cutometers base linear measurements on a set, or pre-determined, time of an inflection point whether or not the inflection point actually occurs that that point in time. In FIG. 10, the Cutometer is set to calculate Ue and Uv based on an inflection point at 0.1 sec. Similarly, the Cutometer is set to calculate Ur based on an inflection point at 1.1 sec. on the relaxation/recovery side. This practice results in further inaccuracies associated with use of the current linear Cutometer parameters for calculating elasticity. Because the inflection point separates elastic deformation from viscous deformation, the inflection point of a particular sample of skin or material is a specific property of the skin or material.

Figure 11:
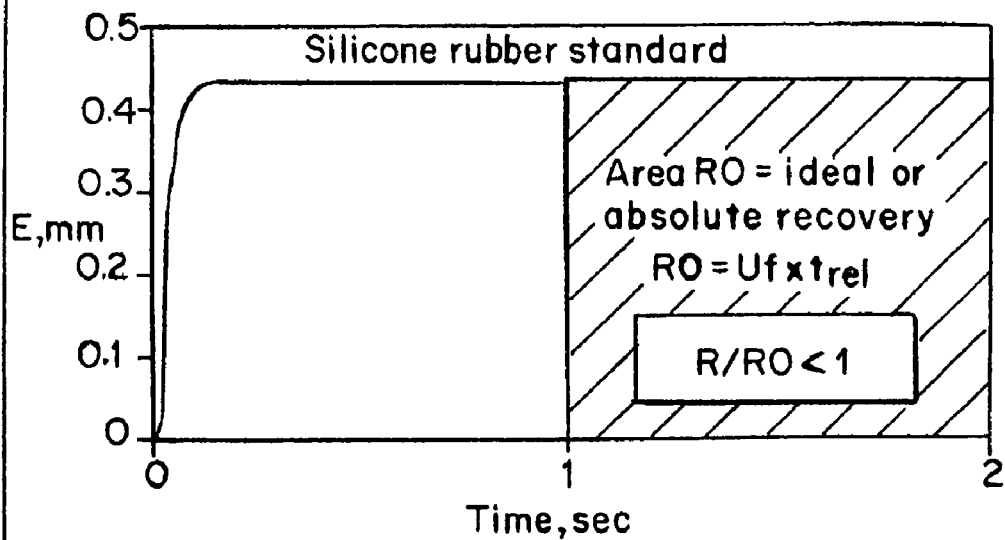
FIG. 11 is a deformation/relaxation Cutometer graph of a silicone standard depicting absolute recovery of a material.

Ideally, materials including skin will completely recover or completely relax after the deformation phase of a Cutometer analysis. The ideal or absolute recovery area, R0, of a silicone standard material is depicted in FIG. 11. This area equals Uf multiplied by the relaxation time. The relaxation time is shown to be 1 second and is equal to the deformation time in the Cutometer analyses discussed herein. However, depending upon the subject or participant undergoing analysis or depending upon the material, it may take longer than 1 second to completely recover from a 1 second deformation event. In keeping the deformation/extension time equal to the relaxation/recovery time direct energy calculations are simplified. The area ratios described herein are expected to be valid upon increasing time to observe the relaxation/recovery period.

Figure 12:
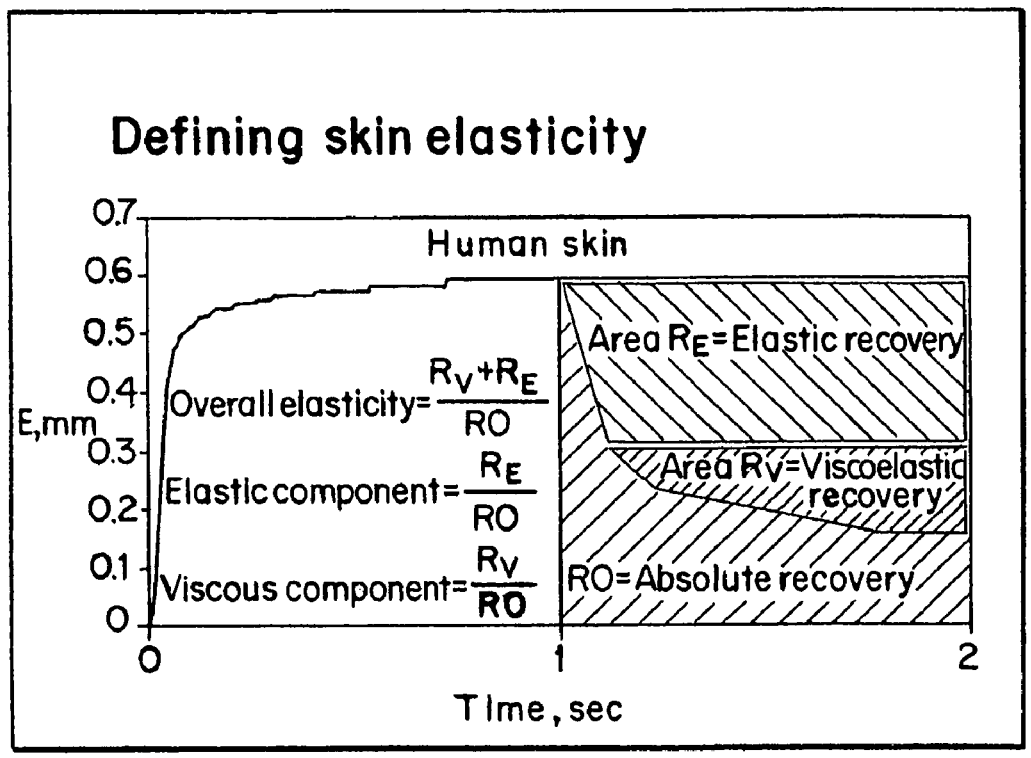
FIG. 12 is a deformation/relaxation Cutometer graph of a human skin sample depicting areas associated with overall elasticity, and the elastic and viscous portions of the area.

Human skin does not have ideal elastic properties like silicone. Therefore, skin achieves only a partial recovery in the time measured by a Cutometer. The recovery achieved by skin is due to elastic recovery as represented by Area $R_E$ in FIG. 12 and viscoelastic recovery Area Rv. From this information, overall elasticity may be defined as $(R_V+R_E)/R0$. The elastic component of the overall elasticity is $R_E/R0$, and the viscous component of the overall elasticity is $R_V/R0$.

Figure 13:
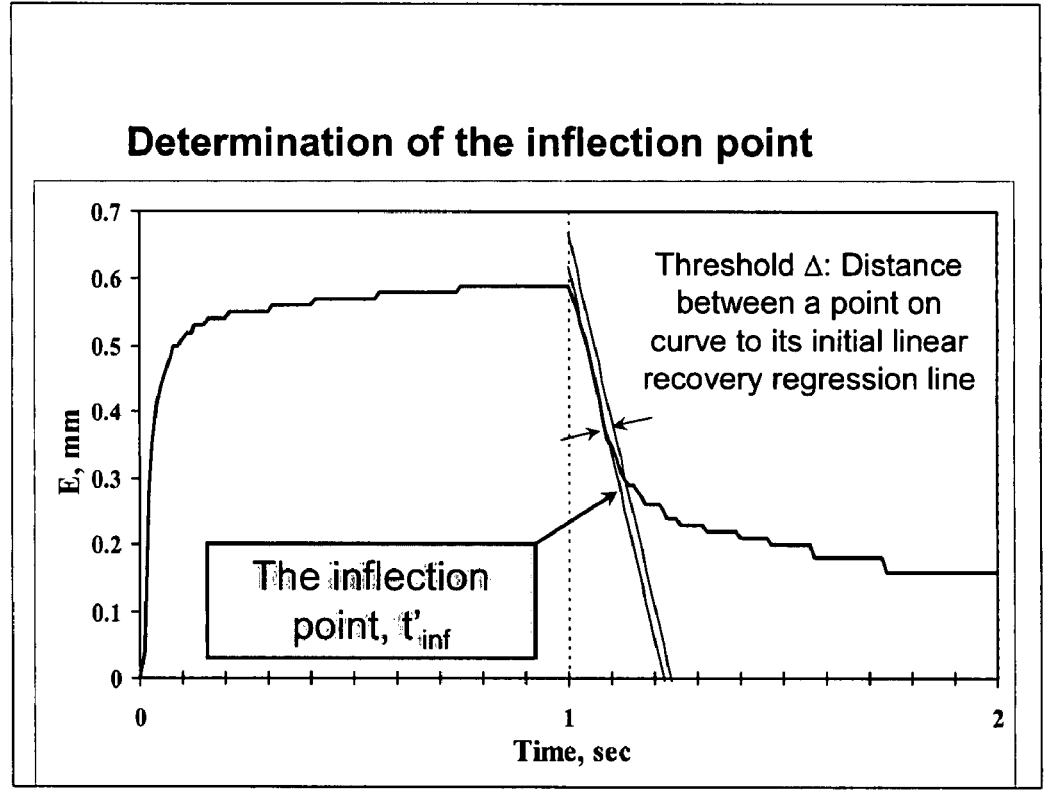
FIG. 13 is a deformation/relaxation Cutometer graph depicting a linear regression line of elastic recovery and threshold line.

Identification of the actual inflection point is the key to the ability to accurately separate the elastic and viscous components of the overall elasticity. To accurately calculate the areas R0, $R_V$ and $R_E$, the actual inflection point along the recovery/relaxation curve must be known. The inflection point of FIG. 13 was determined by establishing a linear regression line along the initial elastic recovery curve. Then a threshold line was defined. The threshold value was determined by experimentation. A macro may be set to allow the threshold to remain variable. Varying threshold values were plugged in one at a time and then its results were compared with the visual effects of the location of the inflection point. A large threshold value would results in an inflection point too far into the curved region of the graph, while too small a threshold value would tend to identify inflection points in the linear region of the graph where some points may not show perfect linear arrangement. The distance between the two lines represents a threshold delta. The inflection point on the curve is the time at which the deviation of the deformation curve from the regression line is greater than the threshold. The inflection point is shown as $t'_{inf}$ in FIG. 13. A computational algorithm was developed to calculate the inflection point in this manner for each Cutometer sample taken.

EXAMPLE 1

Using the area calculations and inflection point identification techniques described herein, a human cheek skin elasticity study was conducted a Cutometer. The study included 430 subjects, both male and female, between the ages of 20 and 70 years. The subjects were of Caucasian, Asian or Hispanic descent.

Figure 14:
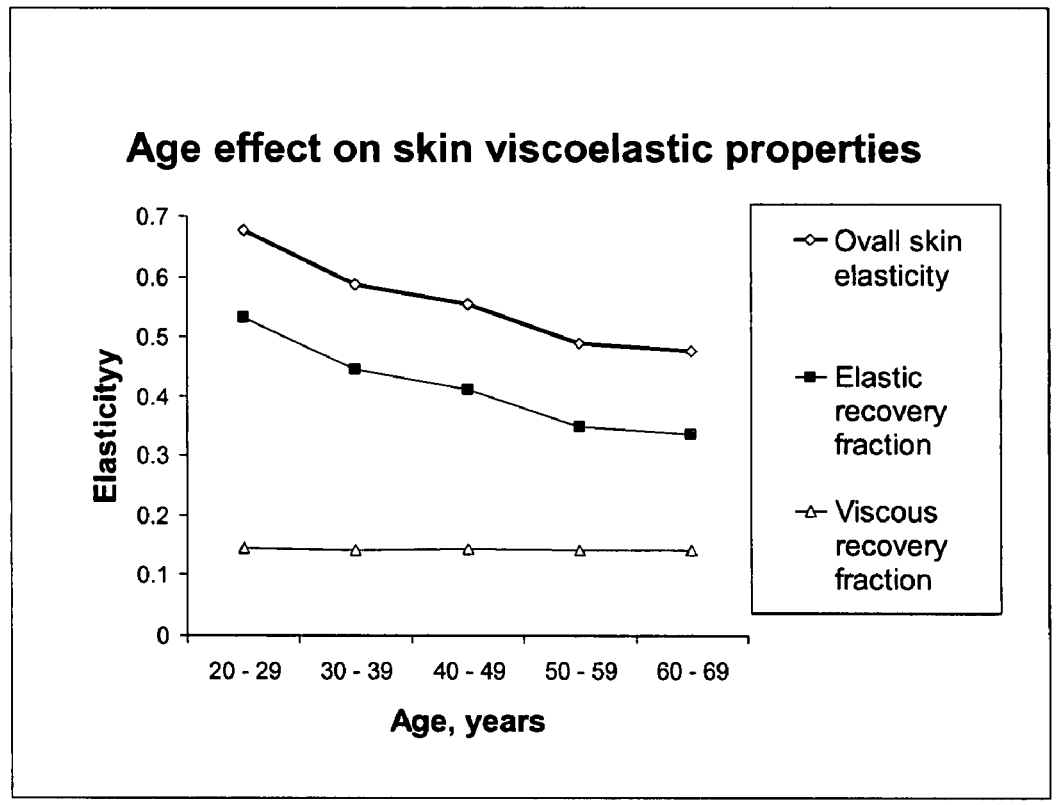
FIG. 14 is a graph depicting the relationship of elasticity as calculated by the area analysis to age.

The overall skin elasticity, $(R_V+R_E)/R0$, the skin's elastic recovery fraction, $R_E/R0$, and the skins viscous recovery fraction, $R_V/R0$, were calculated from the Cutometer curves and plotted against the participant's age. As can be seen in FIG. 14, there is a trend toward a decrease in overall skin elasticity with increased age. This decrease may be attributed to the decrease in the elastic component of the overall elasticity because the viscous component did not change significantly with age. These results are aligned with published results of skin mechanical property studies using Instron on cadaver skins. Instron is a research-grade tensiometer instrument used in many engineering areas. It is classically used to measure various physical and material properties. See the publication by G P Seehra, and F H Silver, "Viscoelastic Properties of Acid- and Alkaline-Treated Human Dermis: and Correlation Between Total Surface Charge and Elastic Modulus." Skin Research and Technology, 2006, 12(3), 190-198. See also the publication by F H Silver, G P Seehra, J W Freeman, and D Devore, "Viscoelastic Properties of Young and Old Human Dermis: A Proposed Molecular Mechanism for Elastic Energy Storage in Collagen and Elastin." Journal of Applied Polymer Science, 2002, 86(8), 1978-1985.

Figure 15:
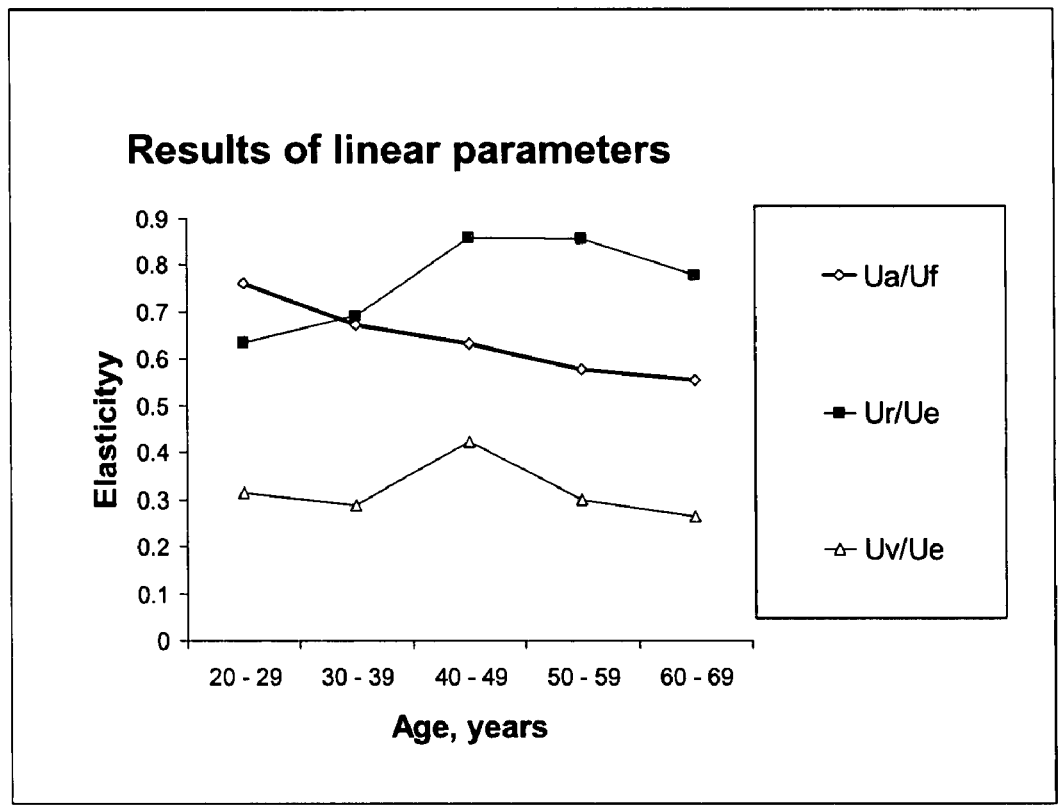
FIG. 15 is a graph depicting the same data represented in FIG. 14 with elasticity calculated by linear parameters as compared to age.

Using conventional, linear parameters rather than the area analysis described herein, the results of the human skin elasticity study would resemble those of FIG. 15. The overall elasticity (Ua/Uf) showed a meaningful trend. However, pure elasticity (Ur/Ue) and viscoelastic ratio (Ur/Ue) showed no meaningful trend. The data from the linear parameters suggests that elasticity improves for a time during middle age and then declines. These results are inconsistent with the generally accepted understanding of the aging process of skin and can be explained by the inaccuracies in the method as discussed hereinabove.

Figure 16:
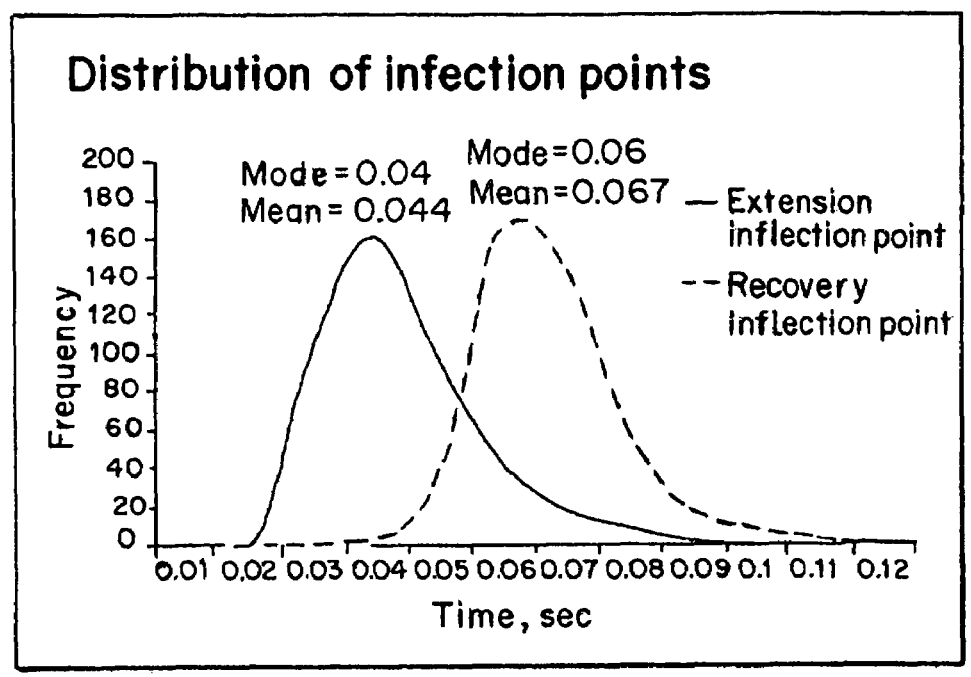
FIG. 16 is a graph depicting the distribution of inflection points determined during the human skin study.

FIG. 16 shows the distribution of the inflection points for the extension/deformation curve (to the left in FIG. 16) and the recovery/relaxation curve (to the right in FIG. 16). The mean inflection points occur at 0.044 seconds, and 0.067 seconds, respectively.

EXAMPLE 2

A Cutometer SEM575 (CK Electronic GmbH) with a 2-mm aperture probe was used in this study. All measurements were taken in the lab under controlled temperature and humidity (20-22° C., 45-50% RH). Using Mode I in which the measurements were conducted with a negative pressure of 400 mbar, with the suction and release times each set at 2 seconds. All measurements were taken in the lab under controlled temperature and humidity (20-22° C., 45-50% relative humidity). Two anti-aging creams, formulas No. 9295-04 and 9295-05, each contained a specific blend of anti-aging ingredients to boost cellular energy, DNA repair, antioxidation and collagen renewal, were used in the investigation. The anti-aging crèmes used, for example, include formulations disclosed in U.S. patent application Ser. No. 11/636,889 filed Dec. 11, 2006 and incorporated herein by reference, and U.S. patent application Ser. No. 11/698,016 filed Jan. 25, 2007 and incorporated herein by reference.

The study was conducted in two parts. In part one, measurements were conducted on the left and right forearms of 69 healthy female volunteers, ages 18 to 60 years old, to construct correlations of skin viscoelastic properties with age. Part two of the study was conducted on a separate group of 30 female volunteers ranging in age between 45 and 60 years old. The volunteers were required to apply two anti-aging products, one on each of their forearms, twice a day for 6 weeks. Cutometer measurements were taken at the baseline (day zero) and after 6 week treatment. Data was analyzed using the novel viscoelastic parameters involving identification of the actual inflection point as described herein. Certain nonconformance data were excluded from calculation.

Figure 17:
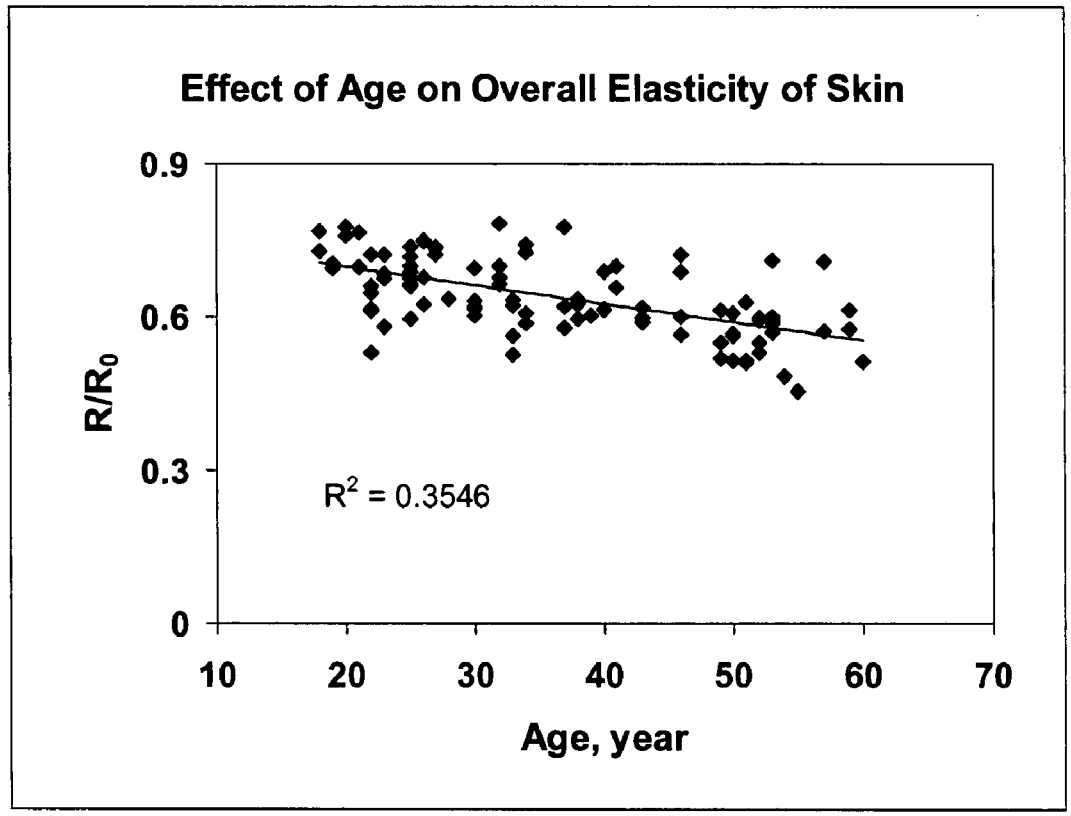
FIG. 17 is a graph depicting the decrease in viscoelastic recovery, $R/R_0$, with increasing age.
Figure 18:
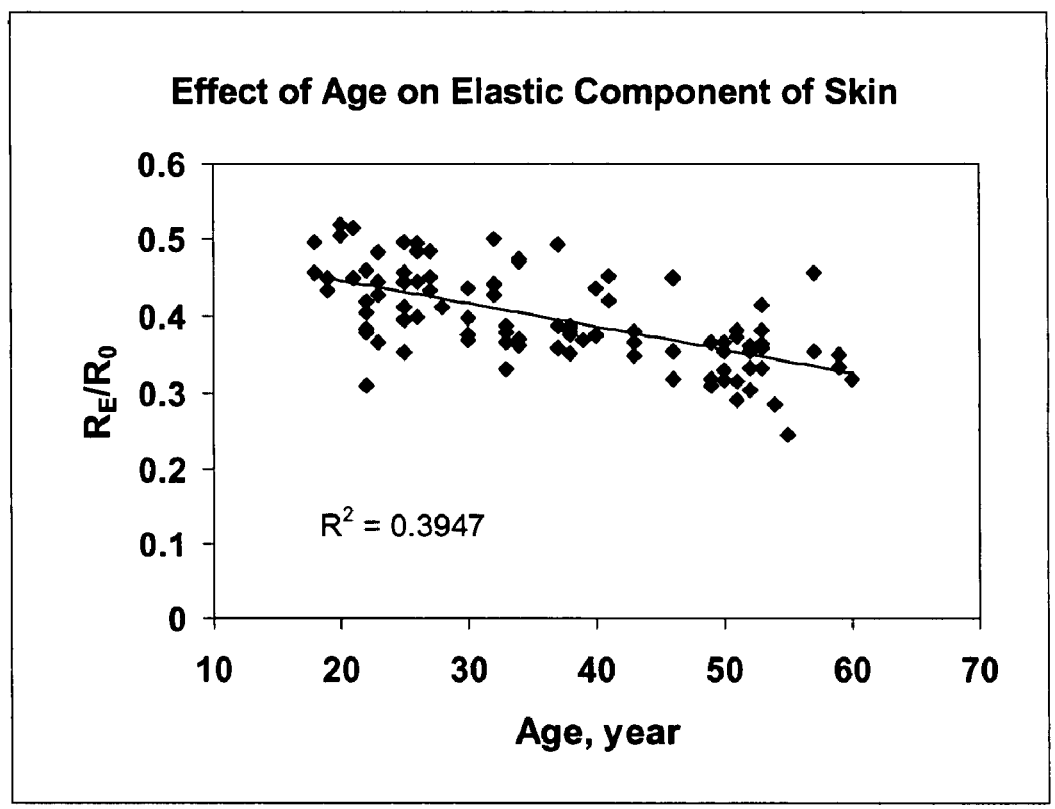
FIG. 18 is a graph depicting the linear decrease of elastic recovery, $R_E/R_0$, with age.
Figure 19:
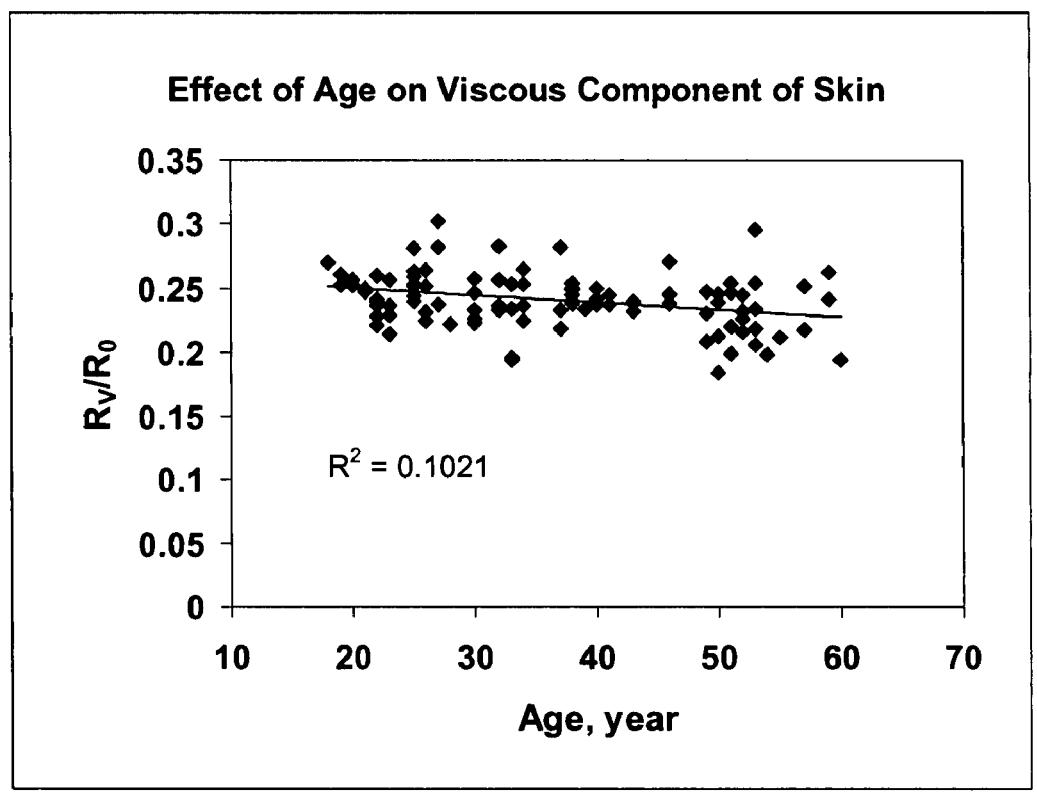
FIG. 19 is a graph depicting the change in the viscous component of the skin, $R_V/R_0$, with increasing age.

A declining trend was observed between age and skin viscoelastic parameters. The total viscoelastic recovery, $R/R_0$, decreased linearly with increase in age, as shown in FIG. 17. This decrease was directly attributed to the linear decrease of $R_E/R_0$ (elastic recovery) over age (FIG. 18) as age did not seem to affect the viscous recovery of the skin although a very slight declining trend was observed (FIG. 19). These trends are in agreement with the results of our previous studies (Qu, D., Seehra, G., and Masotti, C. Novel Method to Evaluate Skin Viscoelastic Properties using Inflection and Area Analysis of Stress-Relaxation Measurement. 2006 U.S. Symposium of ISBS. Atlanta, Ga., USA.; and Qu, D., Masotti, C., and Seehra, G. Effect of Age, Gender, Ethnicity and Sun-Exposure on the Viscoelastic Properties of Skin. 2006 SCC Annual Meeting. New York, N.Y., USA) and are also supported by the general understand about age and skin elastic properties.

Figure 20:
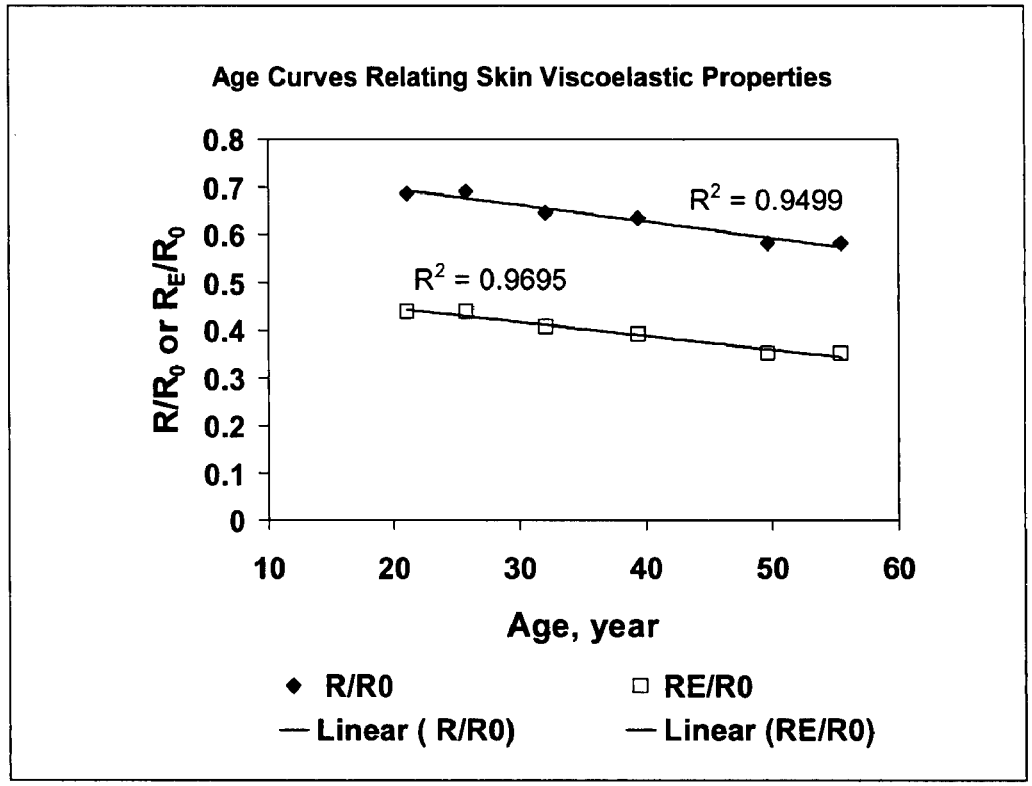
FIG. 20 is a plot of both $R/R_0$ (viscoelastic recovery) and $R_E/R_0$ (elastic recovery) against age.

Linear functions of age versus the two declining viscoelastic parameters were then constructed to predict the mechanical behavior of the skin. These functions served as standard curves to help quantify the efficacy of anti-aging products. To do that, we grouped the volunteers using weighted average age to have relatively uniform distribution of population in each age bracket, as shown in Table 1. The values of $R/R_0$ and $R_E/R_0$ were then plotted against age, as shown in FIG. 20. Excellent correlations are exhibited as indicated by the values of $R^2$.

TABLE 1

Subject Age Group and Number Distribution

| Average Age, years | | | | | |
|---|---|---|---|---|---|
| 21 | 26 | 32 | 39 | 50 | 56 |

| Count | 18 | 16 | 17 | 18 | 19 | 12 |

Figure 21:
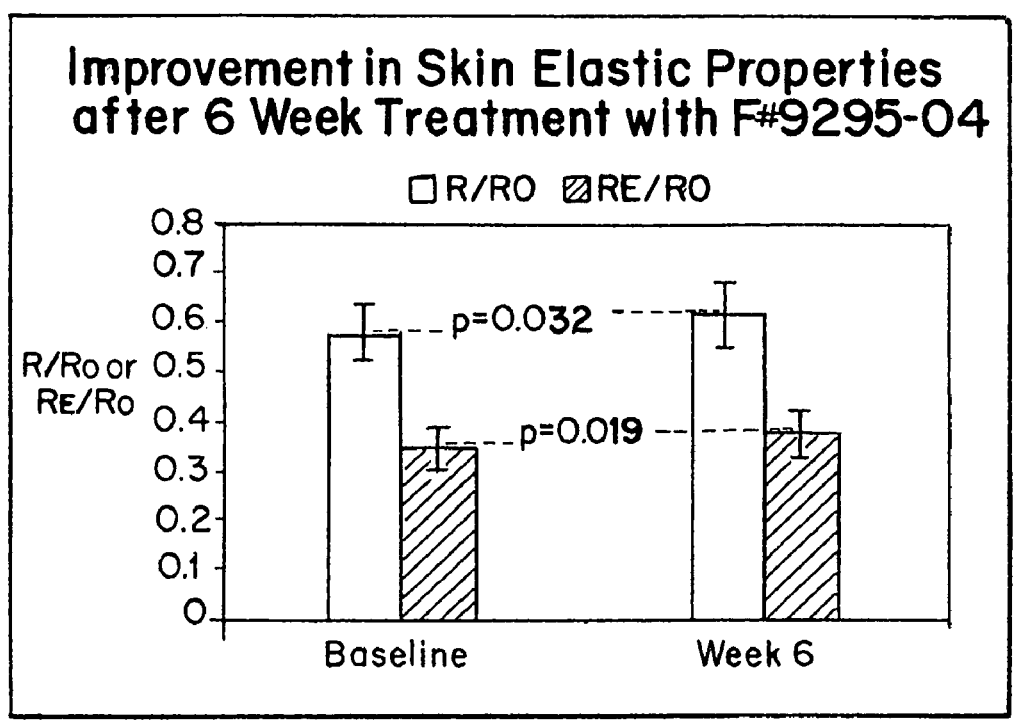
FIG. 21 is a graphic representation of skin elastic properties after six weeks of treatment with formulation F#9295-04.
Figure 22:
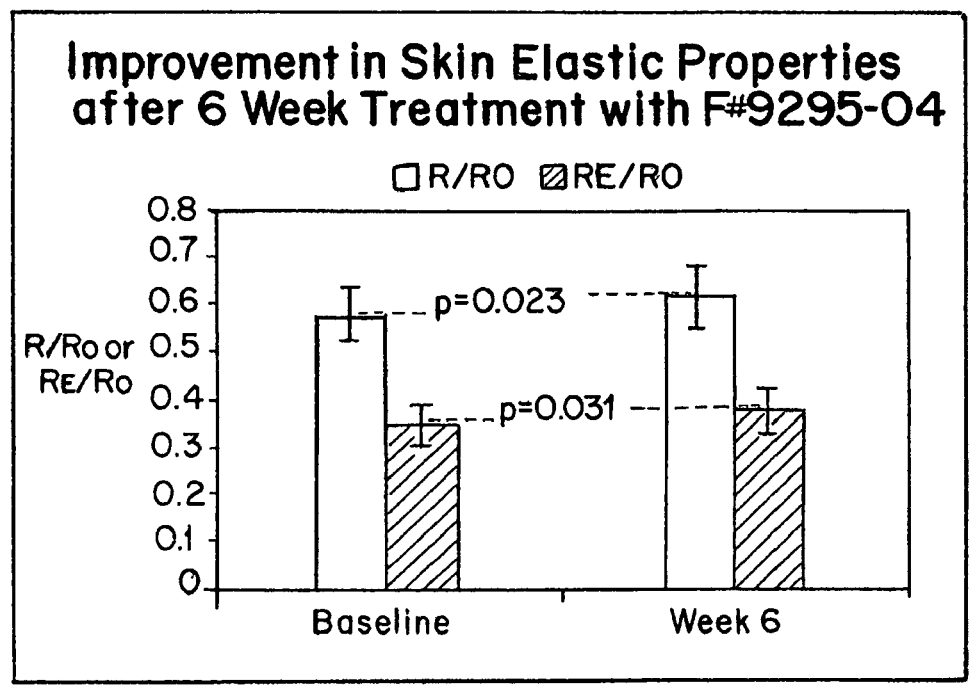
FIG. 22 is a graphic representation of skin elastic properties after six weeks of treatment with formulation F#9295-05.

In the second part of the study, measurements were collected using the Cutometer from the 30 volunteers whose forearms had been treated with two anti-aging creams. Parameters of $R/R_0$ and $R_E/R_0$ were calculated at the baseline (day zero) and after 6 weeks of treatment. Statistically significant improvements in total viscoelastic recovery and elastic recovery ($p<0.05$) were obtained to indicate efficacy of both anti-aging products, formulas No. 9295-04 and 9295-05, as shown in FIGS. 21 and 22, respectively, where the clear bars represent $R/R_0$ and the shaded bars indicate $R_E/R_0$. There was no significant difference in viscoelastic properties between the use of two test products. One important point we would like to convey is that this statistical significance would not have been achieved had the novel viscoelastic parameters not been used.

Figure 23:
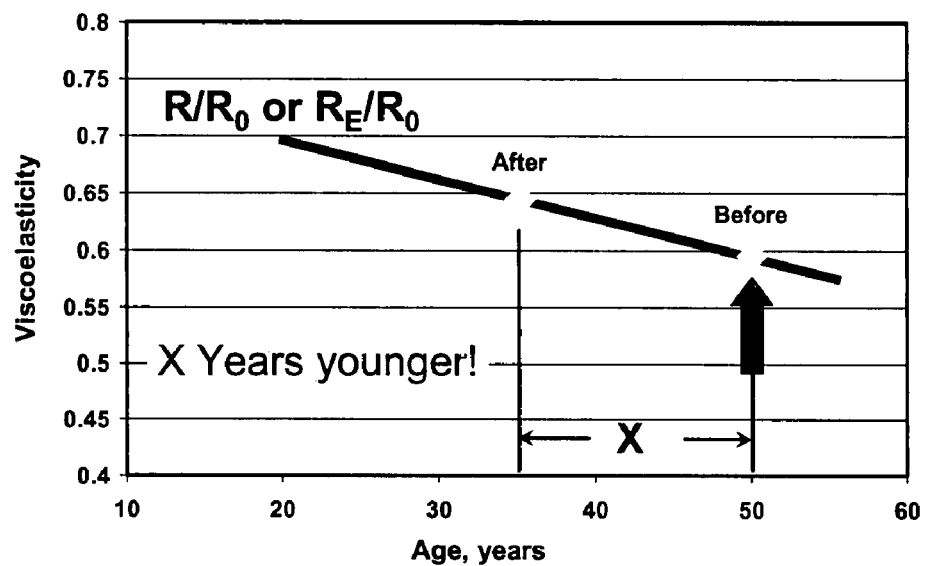
FIG. 23 is a graph depicting how the Cutometer measurements before and after treatment with a skin care composition can be used to determine the benefit of use of the composition.

By taking baseline measurements of different age groups, we can construct a "standard age curve" that displays average viscoelasticity (or elasticity) vs. age as shown in FIG. 23. In a second experiment, we can then use that curve to evaluate the performance of a product and relating it to a "X years younger" claim by the following. We select a specific aged population (e.g. age 48 to 52) and take a baseline "elasticity" measurements, and average that data to produce a mean value that represents elasticity for that average age. Using that same population, we then conduct a product performance study where subjects apply product per dosage recommendations over a certain duration (e.g. 8 weeks), and we re-test "elasticity" (after 8 weeks). If elasticity is shown to increase by 'A' amount on the y axis, we can then correlate that result with 'B' improvement in age on the x axis per the standard age curve we previously constructed. For example, according to the sample curve displayed in FIG. 23, an improvement from 0.6 to 0.65 in viscoelasticity correlates to improvement of 15 years on average—0.6 represents average 50 year old skin and 0.65 represents average 35 year old skin with the difference at 15 years.

Figure 24:
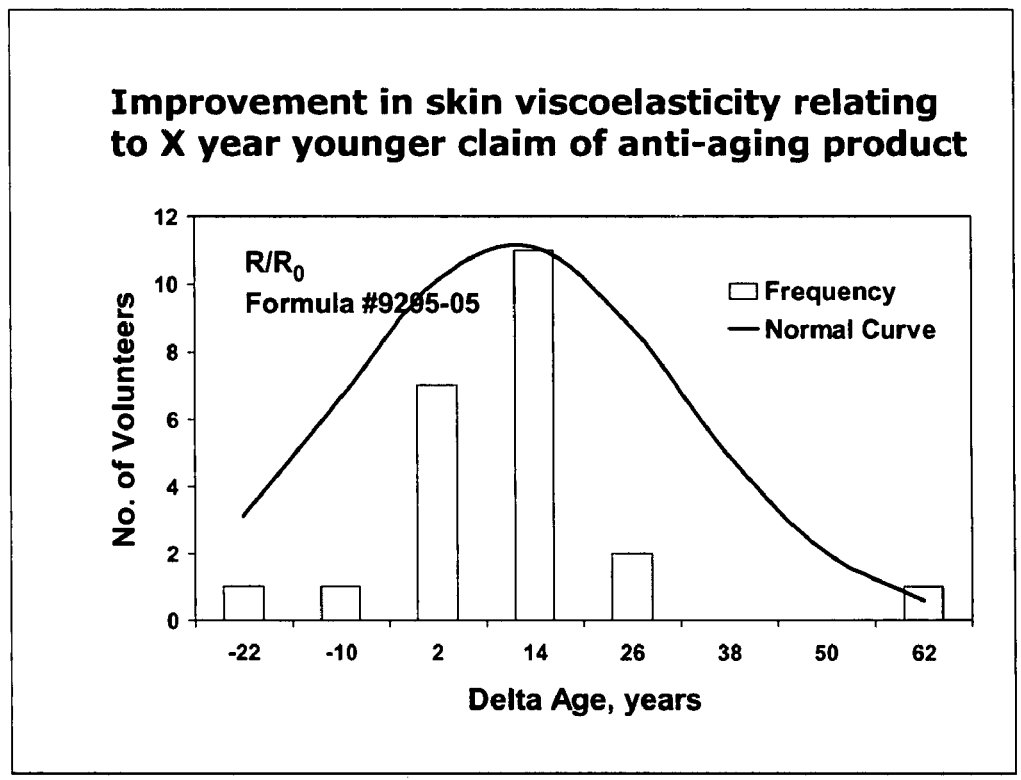
FIG. 24 is a bar graph of the distribution of the apparent age decrease as measured by change in viscoelastic recovery, $R/R_0$, after six weeks treatment with formulation F#9295-05.
Figure 25:
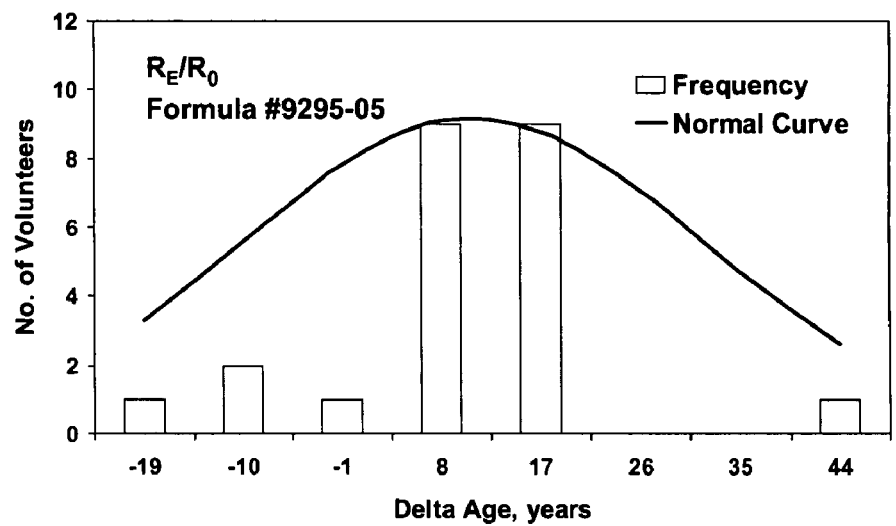
FIG. 25 is a bar graph of the distribution of the apparent age decrease as measured by change in elastic recovery, $R_E/R_0$, after six weeks treatment with formulation F#9295-05.

Using the standard age-elasticity curves established above, we can now compare skin viscoelastic parameters before and after treatment, and quantify changes in mechanical properties on a time scale. For example, the viscoelastic parameters, $R/R_0$ and $R_E/R_0$, obtained at the beginning of the study reflect the true age of a volunteer. This age can be found on the age-elasticity curve shown in FIG. 20. After 6 weeks treatment with an anti-aging product the values of $R/R_0$ and $R_E/R_0$ are measured again and a corresponding age is found again on the standard curve. The difference in these two calculated ages reflects the changes in skin viscoelastic properties relative to age, a quantitative measure of anti-aging efficacy of test product. In this study, parameters of $R/R_0$ and $R_E/R_0$ were calculated for each of the 30 test volunteers, and the distributions of age difference corresponding to each of the viscoelastic parameters are shown in the following histograms in FIGS. 24 and 25. It was clear to see, in average, that the products had improved the mechanical properties of the skin to show apparent ages that were many years younger than the volunteer's true age. The mode of distribution in FIGS. 24 and 25 indicates; those shifts in age occur mostly around 15 years.

It is worth noting that the measurement of the viscous recovery of the skin did not change much with age. The same results were obtained in previous studies of human cheek skin on more than 400 volunteers (Qu, D., Masotti, C., and Seehra, G. Effect of Age, Gender, Ethnicity and Sun-Exposure on the Viscoelastic Properties of Skin. 2006 SCC Annual Meeting. New York, N.Y., USA). It also agrees with an ex-vivo study reported previously (Seehra, G. and Silver, F. Viscoelastic properties of acid- and alkaline-treated human dermis: a correlation between total surface charge and elastic modulus. Skin Res. Technol., 12 (2006) 192-198).

However, since the viscous recovery area (area $R_v$ in FIG. 2) is strictly speaking a combined area of elastic and viscous recovery, the slight declining trend is actually meaningful. It indicates that the elastic component in this combined recovery area is very small and the viscous component dominates the region. Regarding the distribution in calculated age difference (years younger) in FIGS. 24 and 25, the majority of the volunteers responded in the range of 8 to 17 years which is a very good indication of accuracy considering the normal variability of in vivo measurement of viscoelastic properties on biological subjects.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as" or "for example") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise.

What is claimed is:

1. A method of determining a skin elasticity value for the skin of an individual, the method comprising the steps of:
    applying a negative pressure to a skin sample on a person for a preselected first period of time and subsequently releasing the pressure;
    obtaining a deformation curve over the first period of time from the application of the negative pressure
    obtain a relaxation curve over a period of time from an end of the first period of time to a preselected second period of time;
    determining an inflection point on the relaxation curve;
    defining an area associated with an absolute recovery wherein the area is bounded on the left by a vertical representation of a maximum deformation of the skin; bounded on the right by a vertical line through the preselected second period of time; bounded on the top by a horizontal representation of the maximum deformation of the skin; and bounded on the bottom by a horizontal reference point to a position of the skin prior to deformation;
    defining an area associated with elastic recovery wherein the area is bounded on the left by the relaxation curve; bounded on the right by the vertical line through the preselected second period of time; bounded on the top by the horizontal representation of the maximum deformation of the skin; and bounded on the bottom by a horizontal line intersecting the inflection point;
    defining an area associated with a viscoelastic recovery wherein the area is bounded on the left and the bottom by the relaxation curve; bounded on the right by the vertical line through the preselected second period of time; and bounded on the top by the horizontal line intersecting the inflection point; and
    calculating a value associated with an elastic recovery or a viscoelastic recovery or both.

2. The method of claim 1 wherein the elastic recovery is calculated by dividing the area associated with elastic recovery by the area associated with the absolute recovery.

3. The method of claim 1 wherein the viscoelastic recovery is calculated by dividing the area associated with the viscoelastic recovery by the area associated with the absolute recovery.

4. The method of claim 1 further comprising the steps of comparing an elasticity value to a database of known elasticity values compared to age of an individual, and determining an age of the individual.

5. The method of claim 4, wherein the steps for determining the age of the individual from a database comparison is conducted prior to and then after treatment with a topically or orally administered agent for improving skin health.

6. The method of claim 1 wherein the inflection point is determined by establishing a linear regression line along an initial portion of the relaxation curve.

7. A method of determining a skin elasticity value for the skin of an individual comprising:
    using a cutometer to apply a negative pressure to a portion of skin on a person for a preselected first period of time and subsequently releasing the pressure;
    measuring a linear distance that the portion of skin deforms over the first period of time;
    measuring a linear distance that the portion of skin relaxes from the first period of time to a preselected second period of time;
    creating a deformation curve over the first period of time;
    creating a relaxation curve over a period of time from an end of the first period of time to a preselected second period of time;
    determining an inflection point on the relaxation curve using a linear regression line along an initial portion of the relaxation curve;
    defining an area associated with an absolute recovery wherein the area is bounded on the left by a vertical representation of a maximum deformation of the skin; bounded on the right by a vertical line through the preselected second period of time; bounded on the top by a horizontal representation of the maximum deformation of the skin; and bounded on the bottom by a horizontal reference point to a position of the skin prior to deformation;
    defining an area associated with elastic recovery wherein the area is bounded on the left by the relaxation curve; bounded on the right by the vertical line through the preselected second period of time; bounded on the top by the horizontal representation of the maximum deformation of the skin; and bounded on the bottom by a horizontal line intersecting the inflection point;
    defining an area associated with a viscoelastic recovery wherein the area is bounded on the left and the bottom by the relaxation curve; bounded on the right by the vertical line through the preselected second period of time; and bounded on the top by the horizontal line intersecting the inflection point; and
    calculating a value associated with an elastic recovery or a viscoelastic recovery or both.

* * * * *

UNITED STATES PATENT AND TRADEMARK OFFICE
CERTIFICATE OF CORRECTION

PATENT NO. : 7,556,605 B2
APPLICATION NO. : 11/906198
DATED : July 7, 2009
INVENTOR(S) : Di Qu et al.

Page 1 of 1

It is certified that error appears in the above-identified patent and that said Letters Patent is hereby corrected as shown below:

In the Claims

In column 9, claim 1, line 43, before "a relaxation curve" replace "obtain" with --obtaining--.

Signed and Sealed this

Seventeenth Day of November, 2009

David J. Kappos
*Director of the United States Patent and Trademark Office*